United States Patent
Kuang et al.

(10) Patent No.: US 9,241,923 B2
(45) Date of Patent: Jan. 26, 2016

(54) METHODS FOR PROMOTING NEURONAL DEVELOPMENT AND/OR HEALTH

(71) Applicant: Mead Johnson Nutrition Company, Glenview, IL (US)

(72) Inventors: Chenzhong Kuang, Newburgh, IN (US); Yan Xiao, Neburgh, IN (US); Eduard Poels, Newburgh, IN (US); Zeina Jouni, Evansville, IN (US); Dirk Hondmann, Winnetka, IL (US)

(73) Assignee: Mead Johnson Nutrition Company, Glenview, IL (US)

( * ) Notice: Subject to any disclaimer, the term of this patent is extended or adjusted under 35 U.S.C. 154(b) by 35 days.

(21) Appl. No.: 13/942,794

(22) Filed: Jul. 16, 2013

(65) Prior Publication Data

US 2015/0023922 A1    Jan. 22, 2015

(51) Int. Cl.
| | | |
|---|---|---|
| *A61K 31/385* | (2006.01) | |
| *A23L 1/29* | (2006.01) | |
| *A23L 1/30* | (2006.01) | |
| *A61K 31/10* | (2006.01) | |
| *A61K 31/202* | (2006.01) | |
| *A61K 31/7012* | (2006.01) | |
| *A61K 33/30* | (2006.01) | |
| *A61K 35/66* | (2015.01) | |
| *A61K 38/40* | (2006.01) | |
| *A23L 1/304* | (2006.01) | |
| *A23C 9/20* | (2006.01) | |
| *A61K 31/26* | (2006.01) | |
| *A61K 35/741* | (2015.01) | |
| *A23L 1/305* | (2006.01) | |

(52) U.S. Cl.
CPC ............... *A61K 31/385* (2013.01); *A23C 9/20* (2013.01); *A23L 1/296* (2013.01); *A23L 1/30* (2013.01); *A23L 1/304* (2013.01); *A23L 1/3008* (2013.01); *A23L 1/3056* (2013.01); *A61K 31/10* (2013.01); *A61K 31/202* (2013.01); *A61K 31/26* (2013.01); *A61K 31/7012* (2013.01); *A61K 33/30* (2013.01); *A61K 35/66* (2013.01); *A61K 35/741* (2013.01); *A61K 38/40* (2013.01); *A23V 2002/00* (2013.01); *A23V 2200/322* (2013.01)

(58) Field of Classification Search
None
See application file for complete search history.

(56) References Cited

U.S. PATENT DOCUMENTS

| | | | |
|---|---|---|---|
| 5,374,567 A | 12/1994 | Cartagena | |
| 5,397,591 A | 3/1995 | Kyle | |
| 5,550,156 A | 8/1996 | Kyle | |
| 5,849,885 A | 12/1998 | Nuyens | |
| 5,861,491 A | 1/1999 | Nuijens | |
| 5,919,913 A | 7/1999 | Nuyens | |
| 6,620,326 B1 | 9/2003 | Lihme et al. | |
| 6,977,046 B2 | 12/2005 | Hubbuch et al. | |
| 7,368,141 B2 | 5/2008 | Lihme | |
| 7,812,138 B2 | 10/2010 | Lihme et al. | |
| 2005/0107338 A1 | 5/2005 | Seidman | |
| 2008/0003330 A1 | 1/2008 | Rueda et al. | |
| 2010/0104696 A1* | 4/2010 | Banavara et al. | 426/72 |
| 2012/0136220 A1 | 5/2012 | Reynolds | |
| 2012/0184484 A1 | 7/2012 | Wang et al. | |
| 2012/0219526 A1 | 8/2012 | Klassen et al. | |
| 2013/0150306 A1 | 6/2013 | Wittke | |
| 2013/0172286 A1* | 7/2013 | Gil Hernandez et al. | 514/48 |
| 2014/0105875 A1* | 4/2014 | Bolster et al. | 424/93.45 |
| 2014/0161928 A1* | 6/2014 | Hageman | 426/2 |
| 2014/0179775 A1 | 6/2014 | Kuang et al. | |
| 2014/0200195 A1* | 7/2014 | Sijben et al. | 514/54 |

FOREIGN PATENT DOCUMENTS

| | | |
|---|---|---|
| CN | 102318827 | 1/2012 |
| EP | 2258218 | 12/2010 |
| EP | 2609814 | 7/2013 |
| GB | 2327347 | 1/1999 |
| WO | 9200799 | 1/1992 |
| WO | 9717132 | 5/1997 |
| WO | 0218237 | 3/2002 |
| WO | 2014109862 | 7/2014 |

OTHER PUBLICATIONS

Dictionary of Food Science and Technology. Lipoic acid. Docosahexaenoic acid.Lactoferrin.Sialic acid.Wiley-Blackwell (publisher). Second edition. Copyright 2009 International Food Information Service. Editorial Offices, Ames, Iowa. pp. 254, 138, 246, 386.*

Dictionary of Science. Zinc sulphate.Oxford University Press (publisher). Sixth edition. Copyright 2010 Market House Books, Ltd. Editorial Offices, Oxford, UK. p. 887.*

PubChem.alpha-Lipoic acid. Datasheet [online]. NCBI, NIH. Create date: Sep. 16, 2004. [retrieved on Sep. 11, 2014]. Copyright NCBI. NLM.NIH. Bethesda, MD. Retrieved from the Internet: <URL: http://pubchem.ncbi.nlm.nih.gov/summary/summary.cgi?cid=864&loc=ec_rcs>. pp. 1-5.*

(Continued)

*Primary Examiner* — Renee Claytor
*Assistant Examiner* — Sharon M Papciak
(74) *Attorney, Agent, or Firm* — Patterson Intellectual Property Law, P.C.; James R. Cartiglia; Bethany J. Whelan

(57) ABSTRACT

The present disclosure is directed to methods for promoting neuronal health and/or development in a subject by providing nutritional compositions comprising a neurologic component, wherein the neurologic component may promote brain and nervous system development and further provide neurological protection and repair. The neurologic component may include lactoferrin, zinc sulfate, one or more organosulfur compounds, and mixtures thereof.

20 Claims, 5 Drawing Sheets

(5 of 5 Drawing Sheet(s) Filed in Color)

(56) References Cited

OTHER PUBLICATIONS

PubChem. Allyl sulfide. Datasheet [online]. NCBI, NIH. Deposit date: Mar. 21, 2012. [retrieved on Mar. 12, 2015]. Copyright NCBI. NLM.NIH. Bethesda, MD. Retrieved from the Internet: <URL: http://pubchem.ncbi.nlm.nih.gov/compound/cgi?sid=134977839>. pp. 1-3.*

PubChem. Diallyl disulfide. Datasheet [online]. NCBI, NIH. Create date: Mar. 26, 2005. [retrieved on Mar. 9, 2015]. Copyright NCBI. NLM.NIH. Bethesda, MD. Retrieved from the Internet: <URL: http://pubchem.ncbi.nlm.nih.gov/compound/diallyl_sulfide>. pp. 1-3.*

Dictionary of Food Science and Technology. Allyl sulfide.Diallyl disulfide.Sulforaphane.Wiley-Blackwell (publisher). Second edition. Copyright 2009. International Food Information Service. Editorial Offices, Ames, Iowa. p. 15 and 409.*

Borcea, V., et al., "a-Lipoic Acid Decreases Oxidative Stress Even in Diabetic Patients with Poor Glycemic Control and Albuminuria," Free Radical Biology & Medicine, vol. 22, Nos. 11/12, pp. 1495-1500, 1999.

Gleiter, C., et al., "Influence of food intake on the bioavailability of thioctic acid enantiomers," Eur J. Clin. Pharmacol (1996) 50: 513-514.

Harris, J.J., et al., "The Energetics of CNS White Matter," J. Neurosci., Jan. 4, 2012; 32(1): 356-371.

Jordan, S., et al., "A New Metabolic Link. The Acyl carrier protein of lipid synthesis donates lipoic acid to the pyruvate dehydrogenase complex in *Escherichia coli* and Mitochondria," The Journal of Biological Chemistry, vol. 272, No. 29, Issue of Jul. 18, pp. 17903-17906, 1997.

Mehta, S., et al., "Molecular targets in cerebral ischemia for developing novel therapeutics," Brain Research Reviews 54 (2007) 34-66.

Reed, L.J., "Crystalline a-Lipoic Acid: A Catalytic Agent Associated with Pyruvate Dehydrogenase," Science, New Series, vol. 114, No. 2952 (Jul. 27, 1951), pp. 93-94.

Shay, K., et al., "Alpha-Lipoic Acid as a dietary supplement: Molecular mechanisms and therapeutic potential," Biochim Biophys Acta. Oct. 2009; 1790(10): 1149-1160.

Singh, U., et al., "Alpha-Lipoic acid supplementation and diabetes," Nutr Rev. Nov. 2008; 66(11): 646-657.

Packer, L., et al., "Alpha-Lipoic Acid as a Biological Antioxidant," Free Radical Biology & Medicine, vol. 19, No. 2, pp. 227-250, 1995.

Yadomae, T., "Structure and Biological Activities of Fungal B-1, 3-Glucans," Yakugaku Zasshi 2000;120:413-431.

Yamada, T., et al., "a-Lipoic acid (LA) enantiomers protect SH-SY5Y cells against glutathione depletion," Neurochemistry International, 59(7):1003-1009, Dec. 2011.

Ziegler, D., et al., "Treatment of Symptomatic Diabetic Polyneuropathy With the Antioxidant a-Lipoic Acid," Diabetes Care 22:1296-1301, 1999.

MacKenzie, G., et al., "A deficit in zinc availability can cause alterations in tubulin thiol redox status in cultured neurons and in developing fetal rat brain," Free Radical Biology & Medicine 51 (2011) 480-489.

Chauhan, N., et al., "Amelioration of Early Cognitive Deficits by Aged Garlic Extract in Alzheimer's Transgenic Mice," Phytother. Res. 21, 629-640 (2007).

Suchy, J. et al., "Dietary supplementation with a combination of alpha-lipoic acid, acetyl-l-carnitine, glycerophosphocoline, docosahexaenoic acid, and phosphatidylserine reduces oxidative damage to murine brain and improves cognitive performance," Nutrition Research 29 (2009) 70-74.

"Report of the American Institute of Nutrition Ad Hoc Committee on Standards for Nutritional Studies," The Journal of Nutrition, American Society for Nutrition, U.S., vol. 107, No. 7, Jul. 1977.

* cited by examiner

METHODS FOR PROMOTING NEURONAL DEVELOPMENT AND/OR HEALTH

TECHNICAL FIELD

The present disclosure relates to method(s) for promoting neuronal health and development, as well as neurogenesis, in a subject, comprising providing a nutritional composition suitable for administration to adult and pediatric subjects that include a neurologic component. The neurologic component may include lactoferrin, as well as zinc sulfate, at least one organosulfur compound, and combinations thereof. Suitable non-limiting organosulfur compounds include alpha-lipoic acid ("ALA"), allyl sulfide, allyl disulfide, sulforaphane ("SFN"), and/or L-sulforaphane ("L-SFN").

BACKGROUND

The brain makes up only 2% of total body weight, yet it is a demanding organ that uses up to 30% of the day's calories and nutrients. (Harris, J. J. et al, *The Energetics of CNS White Matter*. Jour. of. Neuroscience, January 2012: 32(1): 356-371). The human brain and nervous system begin forming very early in prenatal life and both continue to develop until about the age of three. This early development can have lifelong effects on overall brain and nervous system health. Accordingly, brain nutrients can be important additives in the diets of infants, children and pregnant and lactating women because of their ability to promote early brain development and prevent and protect from brain and nervous system injury or illness. Additionally, brain nutrients are important for adults, as many nutrients promote nervous system repair and provide neuroprotective health benefits.

Numerous nutrients are believed to be involved with supporting healthy brain development. Recently, however, it has been discovered that certain organosulfur compounds, for example ALA, when combined with lactoferrin promote neurogenesis and/or neuronal differentiation on human adipose-derived stem cells ("hADSCs") and human neuronal stem cells ("hNSCs").

Lactoferrin, an iron-binding glycoprotein, is one of the major multifunctional agents present in human milk. It has the capacity to bind two molecules of iron in a reversible fashion and can facilitate the uptake of iron within the intestines.

Zinc Sulfate has the molecular formula $ZnSO_4$. Generally zinc is an essential trace mineral that needs to be provided by the diet. Zinc is required for the biological function of more than 300 enzymes and stabilizes the tertiary structure of some proteins. In the central nervous system, zinc may be concentrated in the synaptic vesicles of specific glutaminergic neurons, which are found primarily in the forebrain and connect with other cerebral structures.

Allyl sulfide, also commonly known as diallyl sulfide is an organosulfur compound with the chemical formula $C_6H_{10}S$. Allyl sulfides, for example diallyl sulfide, diallyl disulfide, and diallyl trisulfide, are principle constituents of garlic oil. In vivo allyl sulfide may be converted to diallyl sulfoxide and diallyl sulfone by cytochrome P450 2E1 (CYP2E1).

Sulforaphane ("SFN") is a molecule within the isothiocyanate group of organosulfur compounds having the molecular formula $C_6H_{11}NOS_2$. SFN and its isomers, for example L-Sulforaphane ("L-SFN"), are known to exhibit anti-cancer and antimicrobial properties in experimental models. SFN may be obtained from cruciferous vegetables, such as broccoli, Brussels sprouts or cabbage. SFN is produced when the enzyme myrosinase reacts with glucoraphanin, a glucosinolate, transforming glucoraphanin into SFN.

What is needed is a method for promoting neuronal health and development, by administering a composition that comprises a neurologic component, in order to support brain and nervous system health. The neurologic component includes lactoferrin, at least one organosulfur compound, and combinations thereof. These nutritional compositions disclosed herein may have additive and/or synergistic nervous system health benefits. Accordingly, the disclosure is directed to methods of promoting and supporting brain and nervous system health by providing a nutritional composition comprising a neurologic component.

BRIEF SUMMARY

Briefly, the present disclosure is directed, in an embodiment, to a method for promoting neuronal development by providing a nutritional composition comprising a neurologic component including lactoferrin, zinc sulfate, at least one organosulfur compound, and/or combinations thereof. Suitable non-limiting examples of organosulfur compounds include ALA, allyl sulfide, allyl disulfide, sulforaphane ("SFN"), and/or L-sulforaphane ("L-SFN").

In certain embodiments the nutritional composition may further comprise a long chain polyunsaturated fatty acid ("LCPUFA"), such as docosahexanoic acid ("DHA"), sialic acid, a prebiotic, a probiotic, β-glucan, an iron source, fisetin, Kaempferol, urosolic acid, or mixtures of one or more thereof.

Due to critical brain development during the first years of life, in one embodiment the method includes providing a nutritional composition which comprises an infant formula or a pediatric nutritional composition that includes the neurologic component described herein. The nutritional compositions described herein may also be useful as medicaments or nutritional supplements for promoting neurological health in subjects with a neural degenerative diseases and/or brain injury. Further, the nutritional compositions of the present disclosure may provide neuroprotective health benefits and promote overall brain and nervous system health.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

The patent or application file contains at least one drawing executed in color. Copies of this patent or patent application publication with color drawing(s) will be provided by the Office upon request and payment of the necessary fee.

DETAILED DESCRIPTION

Figure 1A:
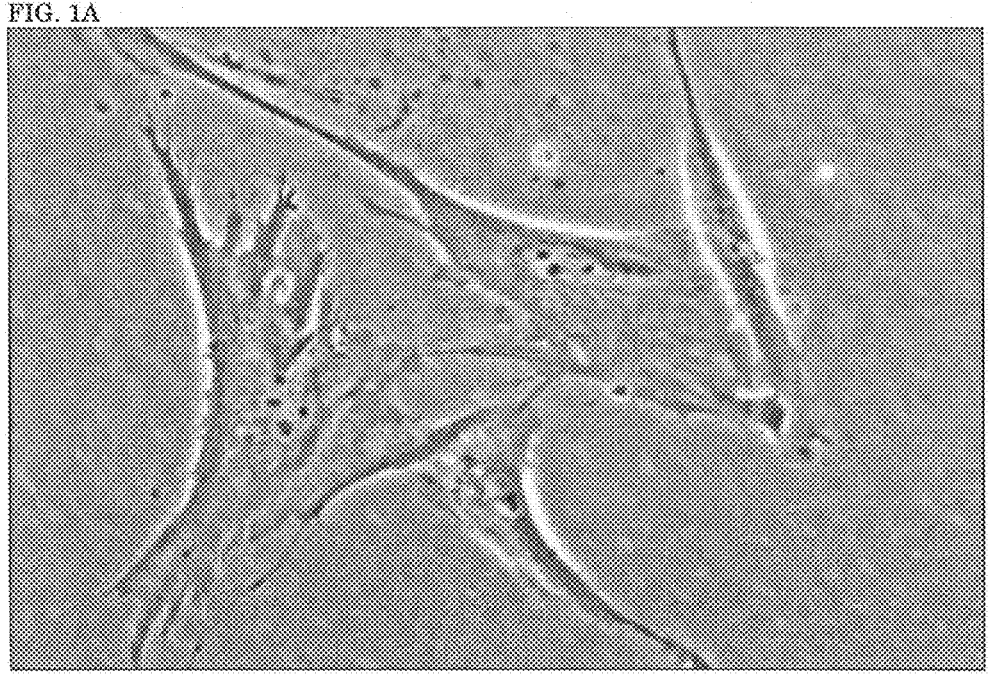
FIG. 1A is a phase contrast microscopy image of hADSCs under the neuronal differentiation condition without treatment of a neurologic component. The morphology of the hADSCs represents a condition of undifferentiation, with a large and flat morphology, as well as no obvious neurite outgrowth.

Reference now will be made in detail to the embodiments of the present disclosure, one or more examples of which are set forth herein below. Each example is provided by way of explanation of the nutritional composition(s) and or methods of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are apparent from the following detailed description. It is to be understood by one of ordinary skill in the art that the present discussion is a description of exemplary embodiments only and is not intended as limiting the broader aspects of the present disclosure.

The present disclosure relates generally to a method for promoting neuronal health and development, by providing a nutritional composition comprising a neurologic component, wherein the neurologic component comprises lactoferrin and an organosulfur compound such as ALA. Additionally, the disclosure relates to methods of supporting and promoting brain and nervous system health, neurogenesis and neuroprotection, and cognitive development by providing a target subject a nutritional composition containing the neurologic component described herein.

"Nutritional composition" means a substance or formulation that satisfies at least a portion of a subject's nutrient requirements. The terms "nutritional(s)", "nutritional formula (s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults. The term "enteral" means deliverable through or within the gastrointestinal, or digestive, tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

A "neurologic component" refers to a compound or compounds, or a composition, that affects neurogenesis, either by promoting or inhibiting neurogenesis. Thus, in some cases, a neurologic component promotes neurogenesis, while in other cases, a neurologic component inhibits or reduces neurogenesis, as compared to the degree of neurogenesis when the neurologic component is not provided.

"Alpha-lipoic acid", abbreviated "ALA" herein, refers to an organosulfur compound derived from octanoic acid having the molecular formula $C_8H_{14}S_2O_2$. Generally, ALA contains two sulfur atoms attached via a disulfide bond. Alpha-lipoic acid is synonymous with lipoic acid, abbreviated "LA", and the two terms and abbreviations may be used interchangeably herein.

As used herein "sulforaphane" includes any known isomers of sulforaphane including but not limited to L-sulforaphane. In some embodiments, sulforaphane may include only L-sulforaphane while, in other embodiments, the reference to sulforaphane may include L-sulforaphane, D-sulforaphane, any other suitable isomer of sulforaphane, and any combinations thereof. Accordingly, the term sulforaphane as used herein includes any isomers of sulforaphane including, but not limited to, stereoisomers, optical isomers, structural isomers, enantiomers, geometric isomers, and combinations thereof.

The term "degree of hydrolysis" refers to the extent to which peptide bonds are broken by a hydrolysis method. For example, the protein equivalent source of the present disclosure may, in some embodiments comprise hydrolyzed protein having a degree of hydrolysis of no greater than 40%. For this example, this means that at least 40% of the total peptide bonds have been cleaved by a hydrolysis method.

The term "partially hydrolyzed" means having a degree of hydrolysis which is greater than 0% but less than 50%.

The term "extensively hydrolyzed" means having a degree of hydrolysis which is greater than or equal to 50%.

"Pediatric subject" means a human less than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or fullterm) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, and preterm infants. "Preterm" means an infant born before the end of the $37^{th}$ week of gestation. "Full term" means an infant born after the end of the $37^{th}$ week of gestation.

"Child" means a subject ranging in age from 12 months to about 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Probiotic" means a microorganism with low or no pathogenicity that exerts at least one beneficial effect on the health of the host.

The term "inactivated probiotic" means a probiotic wherein the metabolic activity or reproductive ability of the referenced probiotic organism has been reduced or destroyed. The "inactivated probiotic" does, however, still retain, at the cellular level, at least a portion its biological glycol-protein and DNA/RNA structure. As used herein, the term "inactivated" is synonymous with "non-viable". More specifically, a non-limiting example of an inactivated probiotic is inactivated *Lactobacillus rhamnosus* GG ("LGG") or "inactivated LGG".

The term "cell equivalent" refers to the level of non-viable, non-replicating probiotics equivalent to an equal number of viable cells. The term "non-replicating" is to be understood as the amount of non-replicating microorganisms obtained from the same amount of replicating bacteria (cfu/g), including inactivated probiotics, fragments of DNA, cell wall or cytoplasmic compounds. In other words, the quantity of non-living, non-replicating organisms is expressed in terms of cfu as if all the microorganisms were alive, regardless whether they are dead, non-replicating, inactivated, fragmented etc.

"Prebiotic" means a non-digestible food ingredient that beneficially affects the host by selectively stimulating the growth and/or activity of one or a limited number of bacteria in the digestive tract that can improve the health of the host.

"β-glucan" means all β-glucan, including specific types of β-glucan, such as β-1,3-glucan or β-1,3;1,6-glucan. Moreover, β-1,3;1,6-glucan is a type of β-1,3-glucan. Therefore, the term "β-1,3-glucan" includes β-1,3;1,6-glucan.

As used herein, "non-human lactoferrin" means lactoferrin which is produced by or obtained from a source other than human breast milk. In some embodiments, non-human lactoferrin is lactoferrin that has an amino acid sequenoic that is different than the amino acid sequence of human lactoferrin. In other embodiments, non-human lactoferrin for use in the present disclosure includes human lactoferrin produced by a genetically modified organism. The term "organism", as used herein, refers to any contiguous living system, such as animal, plant, fungus or micro-organism.

All percentages, parts and ratios as used herein are by weight of the total formulation, unless otherwise specified.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

The development of the brain and nervous system plays a crucial role in the overall health and well-being of an individual. Accordingly, the method(s) of the present disclosure promotes brain and nervous system health. In certain embodiments, the method(s) includes providing the combination of the neurologic component and docosohexaenoic acid ("DHA"), which may have additive and/or synergistic beneficial effects that support brain and nervous system development and health.

As noted above, the neurologic component comprises lactoferrin, zinc sulfate, at least one organosulfur compound, and combinations thereof. Suitable non-limiting organosulfur compounds include alpha-lipoic acid ("ALA"), allyl sulfide, allyl disulfide, sulforaphane ("SFN"), and/or L-sulforaphane ("L-SFN"), and mixtures thereof.

As noted, the neurologic component comprises lactoferrin. Lactoferrins are single chain polypeptides of about 80 kD containing 1-4 glycans, depending on the species. The 3-D structures of lactoferrin of different species are similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion (Fe3+) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms.

Lactoferrin for use in the present disclosure may be, for example, isolated from the milk of a non-human animal or produced by a genetically modified organism. More specifically, the lactoferrin for use herein can, in some embodiments comprise non-human lactoferrin, non-human lactoferrin produced by a genetically modified organism and/or human lactoferrin produced by a genetically modified organism.

Suitable non-human lactoferrins for use in the present disclosure include, but are not limited to, those having at least 48% homology with the amino acid sequence of human lactoferrin. For instance, bovine lactoferrin ("bLF") has an amino acid composition which has about 70% sequence homology to that of human lactoferrin. In some embodiments, the non-human lactoferrin has at least 65% homology with human lactoferrin and in some embodiments, at least 75% homology. Non-human lactoferrins acceptable for use in the present disclosure include, without limitation, bLF, porcine lactoferrin, equine lactoferrin, buffalo lactoferrin, goat lactoferrin, murine lactoferrin and camel lactoferrin.

bLF suitable for the present disclosure may be produced by any method known in the art. For example, in U.S. Pat. No. 4,791,193, incorporated by reference herein in its entirety, Okonogi et al. discloses a process for producing bovine lactoferrin in high purity. Generally, the process as disclosed includes three steps. Raw milk material is first contacted with a weakly acidic cationic exchanger to absorb lactoferrin followed by the second step where washing takes place to remove nonabsorbed substances. A desorbing step follows where lactoferrin is removed to produce purified bovine lactoferrin. Other methods may include steps as described in U.S. Pat. Nos. 7,368,141, 5,849,885, 5,919,913 and 5,861,491, the disclosures of which are all incorporated by reference in their entirety.

In certain embodiments, lactoferrin utilized in the present disclosure may be provided by an expanded bed absorption ("EBA") process for isolating proteins from milk sources. EBA, also sometimes called stabilized fluid bed adsorption, is a process for isolating a milk protein, such as lactoferrin, from a milk source comprises establishing an expanded bed adsorption column comprising a particulate matrix, applying a milk source to the matrix, and eluting the lactoferrin from the matrix with an elution buffer comprising about 0.3 to about 2.0 M sodium chloride. Any mammalian milk source may be used in the present processes, although in particular embodiments, the milk source is a bovine milk source. The milk source comprises, in some embodiments, whole milk, reduced fat milk, skim milk, whey, casein, or mixtures thereof.

In particular embodiments, the target protein is lactoferrin, though other milk proteins, such as lactoperoxidases or lactalbumins, also may be isolated. In some embodiments, the process comprises the steps of establishing an expanded bed adsorption column comprising a particulate matrix, applying a milk source to the matrix, and eluting the lactoferrin from the matrix with about 0.3 to about 2.0M sodium chloride. In other embodiments, the lactoferrin is eluted with about 0.5 to about 1.0 M sodium chloride, while in further embodiments, the lactoferrin is eluted with about 0.7 to about 0.9 M sodium chloride.

The expanded bed adsorption column can be any known in the art, such as those described in U.S. Pat. Nos. 7,812,138, 6,620,326, and 6,977,046, the disclosures of which are hereby incorporated by reference herein. In some embodiments, a milk source is applied to the column in an expanded mode, and the elution is performed in either expanded or packed mode. In particular embodiments, the elution is performed in an expanded mode. For example, the expansion ratio in the expanded mode may be about 1 to about 3, or about 1.3 to about 1.7. EBA technology is further described in international published application nos. WO 92/00799, WO 02/18237, WO 97/17132, which are hereby incorporated by reference in their entireties.

The isoelectric point of lactoferrin is approximately 8.9. Prior EBA methods of isolating lactoferrin use 200 mM sodium hydroxide as an elution buffer. Thus, the pH of the system rises to over 12, and the structure and bioactivity of lactoferrin may be comprised, by irreversible structural changes. It has now been discovered that a sodium chloride solution can be used as an elution buffer in the isolation of lactoferrin from the EBA matrix. In certain embodiments, the sodium chloride has a concentration of about 0.3 M to about 2.0 M. In other embodiments, the lactoferrin elution buffer has a sodium chloride concentration of about 0.3 M to about 1.5 M, or about 0.5 m to about 1.0 M.

The lactoferrin that is employed herein may, in some embodiments, be lactoferrin isolated from whole milk and/or milk having a low somatic cell count, wherein "low somatic cell count" refers to a somatic cell count less than 200,000 cells/mL. By way of example, suitable lactoferrin is available from Tatua Co-operative Dairy Co. Ltd., in Morrinsville, New Zealand, from FrieslandCampina Domo in Amersfoort, Netherlands or from Fonterra Co-Operative Group Limited in Auckland, New Zealand.

Surprisingly, lactoferrin included herein maintains certain bactericidal activity even if exposed to a low pH (i.e., below about 7, and even as low as about 4.6 or lower) and/or high temperatures (i.e., above about 65° C., and as high as about 120° C.), conditions which would be expected to destroy or severely limit the stability or activity of human lactoferrin. These low pH and/or high temperature conditions can be expected during certain processing regimen for nutritional compositions of the types described herein, such as pasteurization. Therefore, even after processing regimens, lactoferrin has bactericidal activity against undesirable bacterial pathogens found in the human gut.

When included as an element of a neurologic component and incorporated into a nutritional composition for practicing the method of the present disclosure, in some embodiments lactoferrin is present in an amount from about 10 mg/100 kcal to about 250 mg/100 kcal. In some embodiments, lactoferrin is present in an amount of from about 50 mg/100 kcal to about 175 mg/100 kcal. In still some embodiments, lactoferrin is present in an amount of from about 100 mg/100 kcal to about 150 mg/100 kcals.

Zinc sulfate may, in some embodiments, be included in the neurologic component of the nutritional composition. In some embodiments, zinc sulfate may be present in the nutritional composition in an amount from about 0.01 mg/100 kcals to about 2 mg/100 kcals. In still other embodiments, zinc sulfate may be present in the nutritional composition from about 0.1 mg/100 kcals to about 1.5 mg/100 kcals. Still, in other embodiments zinc sulfate may be present in the nutritional composition in an amount from about 0.5 mg/100 kcals to about 1.0 mg/100 kcals.

In some embodiments, the at least one organosulfur compound incorporated into the neurologic component may comprise ALA. Examples of ALA suitable for use as the neurologic component include, but are not limited to, enantiomers and racemic mixtures of ALA, including, R-lipoic acid "RLA", S-lipoic acid "SLA", and R/S-LA. Also suitable is R-lipoic acid stabilized with either sodium ("Na-RALA") or potassium as Potassium-R-Lipoate.

When incorporated into a nutritional composition for practicing the method of the present disclosure, ALA may be present, in some embodiments in an amount from about 0.1 mg/100 kcals to about 35 mg/100 kcals. In some embodiments, ALA may be present in an amount from about 2.0 mg/100 kcals to about 25 mg/100 kcals. In still other embodiments, ALA may be present in an amount from about 5.0 mg/100 kcals to about 15 mg/100 kcals.

In some embodiments, organosulfur compound of the neurologic component may comprise allyl disulfide. Allyl disulfide may be present in the nutritional composition, in some embodiments, in an amount from about 1 mg/100 kcals to about 170 mg/100 kcals. In still some embodiments, allyl disulfide may be present from about 50 mg/100 kcals to about 120 mg/100 kcals. In still other embodiments, allyl disulfide may be present from about 75 mg/100 kcals to about 100 mg/100 kcals.

Sulforaphane, which includes L-sulforaphane, may be incorporated into the nutritional composition in an amount from about 1.5 mg/100 kcals to about 7.5 mg/100 kcals. Still in some embodiments, sulforaphane may be present in an amount from about 2 mg/100 kcals to about 6 mg/100 kcals. In some embodiments, sulforaphane may be present in an amount from about 3 mg/100 kcals to about 5 mg/100 kcals.

The nutrients included in the neurologic component of the nutritional composition may be formulated with other ingredients in the nutritional composition to provide appropriate nutrient levels for the target subject. In some embodiments, the nutritional composition comprising a neurologic component is a nutritionally complete formula that is suitable to support normal growth and also benefit brain development. In certain other embodiments, the composition and concentration of the nutrients in the neurologic component are designed to mimic levels that are healthy for early human development.

The nutrients of the neurological component included in the nutritional composition may include functional equivalents, sources, metabolites, prerequisites, and/or combinations thereof. Such nutrients of the neurological component may be naturally-occurring, synthetic, or developed through the genetic manipulation of organisms and/or plants, whether such source is now known or developed later.

The source for the nutrients of the neurologic component described herein may be milk, other dairy products, soybean, meats, eggs, cod, brewer's yeast, organ meats, wheat germ, sugarcane extract, tomatoes, broccoli, Brussels sprouts, cabbage, cauliflower, bok choy, kale, collards, Chinese broccoli, broccoli raab, kohlrabi, mustard, turnip, radish, arugula, watercress, other plants and any other resources, fortified or not, from which the nutrients of the neurologic component could be obtained and used in a nutritional composition. Preferably, the source for the nutrients of the neurologic component should be food grade, having been food derived or microorganism produced. Additionally, the source of the nutrients of the neurologic component could be part of a complex mixture obtained by separation and purification technology known in the art aimed at enrichment of the derivatives or precursors of the neurologic component nutrient of such mixtures.

Further, some amounts of the nutrients in the neurologic component may be inherently present in known ingredients, such as natural oils, carbohydrate sources or protein sources that are commonly used to make nutritional compositions. In some embodiments, the concentrations and ratios as described herein of the neurologic component are calculated based upon both added and inherent sources of the neurological component.

In the methods described herein, as noted, the neurologic component may be formulated with other ingredients to provide a nutritional composition, in order to provide appropriate nutrient levels for the target subject. In some embodiments, the nutritional composition is a nutritionally complete formula that is suitable to support normal growth and also benefit brain development.

Additionally, the neurologic component may be added or incorporated into the nutritional composition by any method well known in the art. In some embodiments, they may be added to a nutritional composition to supplement the nutritional composition. For example, in one embodiment, the neurological component may be added to a commercially available infant formula. For example, Enfalac, Enfamil®, Enfamil® Premature Formula, Enfamil® with Iron, Enfamil® LIPIL®, Lactofree®, Nutramigen®, Pregestimil®, and ProSobee® (each of which is available from Mead Johnson Nutrition Company, Glenview, Ill., U.S.) may be supplemented with suitable levels of the neurologic component, and used in the practice of the present disclosure.

In other embodiments, the neurologic component may be substituted for another nutrient source that does not contain the neurologic component. For example, a certain amount of a fat source may be substituted with another fat source that contains the neurological component. In still other embodiments, the source of an ingredient typically added to a nutritional composition may be altered, such that the source chosen provides both the ingredient that is commonly added to the nutritional composition and the neurological composition.

In some embodiments, the neurologic component may be included in prenatal dietary supplements by any method known in the art. The prenatal administration of the neurologic component may directly impact the development of the fetus and embryo. Since brain development begins early in prenatal life, the inclusion of the neurologic component in a prenatal dietary supplement may promote brain development and neurogenesis in pediatric subjects while still in utero.

Conveniently, commercially available prenatal dietary supplements and/or prenatal nutritional products may be used. For example, Expecta® Supplement (available from Mead Johnson Nutrition Company, Glenview, Ill., U.S.) may be supplemented with suitable levels of the neurologic component and used in practice of the present disclosure.

The prenatal dietary supplement may be administered in one or more doses daily. In some embodiments, the prenatal dietary supplement is administered in two doses daily. In a separate embodiment, the prenatal dietary supplement is administered in three daily doses. The prenatal dietary supplement may be administered to either pregnant women or women who are breastfeeding.

Any orally acceptable dosage form is contemplated by the present disclosure. Examples of such dosage forms include, but are not limited to pills, tablets, capsules, soft-gels, liquids, liquid concentrates, powders, elixirs, solutions, suspensions, emulsions, lozenges, beads, cachets, and combinations thereof. Alternatively, the prenatal dietary supplement of the present disclosure may be added to a more complete nutritional composition. In this embodiment, the nutritional composition may contain protein, fat, and carbohydrate components and may be used to supplement the diet or may be used as the sole source of nutrition.

In some embodiments, the nutritional composition comprises at least one carbohydrate source. The carbohydrate source can be any used in the art, e.g., lactose, glucose, fructose, corn syrup solids, maltodextrins, sucrose, starch, rice syrup solids, and the like. The amount of the carbohydrate component in the nutritional composition typically can vary from between about 5 g/100 kcal and about 25 g/100 kcal. In some embodiments, the amount of carbohydrate is between about 6 g/100 kcal and about 22 g/100 kcal. In other embodiments, the amount of carbohydrate is between about 12 g/100 kcal and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

Moreover, the nutritional composition(s) of the disclosure may comprise at least one protein source. The protein source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate), soy bean proteins, and any combinations thereof.

In a particular embodiment of the nutritional composition, the whey:casein ratio of the protein source is similar to that found in human breast milk. In an embodiment, the protein source comprises from about 40% to about 85% whey protein and from about 15% to about 60% casein.

In some embodiments, the nutritional composition comprises between about 1 g to about 7 g of a protein source per 100 kcal. In other embodiments, the nutritional composition comprises between about 3.5 g to about 4.5 g of protein per 100 kcal.

In some embodiments, the proteins of the nutritional composition are provided as intact proteins. In other embodiments, the proteins are provided as a combination of both intact proteins and hydrolyzed proteins. In certain embodiments, where the protein source comprises hydrolyzed proteins, the hydrolyzed proteins may have a degree of hydrolysis of between about 4% and 10%. In certain other embodiments, the proteins are more hydrolyzed.

In some embodiments, the protein source of the nutritional composition may comprise partially hydrolyzed protein, extensively hydrolyzed protein, and/or combinations thereof. In some embodiments, the proteins that are subjected to a suitable hydrolysis process to provide the protein source disclosed herein are include protein from cow's milk. The proteins may be treated with enzymes to break down some or most of the proteins that cause adverse symptoms with the goal of reducing allergic reactions, intolerance, and sensitization. In still another embodiment, the protein component of the nutritional composition consists essentially of extensively hydrolyzed protein in order to minimize the occurrence of food allergy. Moreover, the proteins may be hydrolyzed by any method known in the art.

In still other embodiments, the protein source comprises amino acids. In yet another embodiment, the protein source may be supplemented with glutamine-containing peptides.

In some embodiments, the nutritional composition of the present disclosure is substantially free of intact proteins. In this context, the term "substantially free" means that the preferred embodiments herein comprise sufficiently low concentrations of intact protein to thus render the formula hypoallergenic. The extent to which a nutritional composition in accordance with the disclosure is substantially free of intact proteins, and therefore hypoallergenic, is determined by the August 2000 Policy Statement of the American Academy of Pediatrics in which a hypoallergenic formula is defined as one which in appropriate clinical studies demonstrates that it does not provoke reactions in 90% of infants or children with confirmed cow's milk allergy with 95% confidence when given in prospective randomized, double-blind, placebo-controlled trials.

The nutritional composition may be protein-free in some embodiments and comprise free amino acids as a protein equivalent source. In some embodiments, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In certain other embodiments, small amino acid peptides may be included as the protein component of the nutritional composition. Such small amino acid peptides may be naturally occurring or synthesized. The amount of free amino acids in the nutritional composition may vary from about 1 g/100 kcal to about 5 g/100 kcal.

The nutritional composition may also comprise a fat source. Suitable fat or lipid sources for the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

The nutritional composition of the present disclosure may also contain a source of long chain polyunsaturated fatty acids ("LCPUFAs"). Suitable LCPUFAs include, but are not limited to DHA, eicosapentaenoic acid ("EPA"), arachidonic acid ("ARA"), linoleic (18:2 n-6), γ-linolenic (18:3 n-6), dihomo-γ-linolenic (20:3 n-6) acids in the n-6 pathway, α-linolenic (18:3 n-3), stearidonic (18:4 n-3), eicosatetraenoic (20:4 n-3), eicosapentaenoic (20:5 n-3), and docosapentaenoic (22:6 n-3), and combinations thereof. Indeed, it is believed there may be a positive synergistic effect in the combination of the neurologic component and DHA.

The amount of LCPUFA in the nutritional composition, in some embodiments, is from about 5 mg/100 kcal to about 100 mg/100 kcal. In still other embodiments, the amount of LCPUFA in the nutritional composition is from about 10 mg/100 kcal to about 50 mg/100 kcal.

Sources of LCPUFAs include dairy products like eggs and butterfat; marine oils, such as cod, menhaden, sardine, tuna and many other fish; certain animal fats, lard, tallow and microbial oils such as fungal and algal oils, or from any other resource fortified or not, form which LCPUFAs could be obtained and used in a nutritional composition. The LCPUFA could be part of a complex mixture obtained by separation technology known in the art aimed at enrichment of LCPUFAs and the derivatives or precursors of LCPUFAs in such mixtures.

The LCPUFAs may be provided in the nutritional composition in the form of esters of free fatty acids; mono-, di- and tri-glycerides; phosphoglyerides, including lecithins; and/or mixtures thereof. Additionally, LCPUFA may be provided in the nutritional composition in the form of phospholipids, especially phosphatidylcholine.

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the weight ratio of ARA:DHA is from about 1:2 to about 4:1.

DHA is present in the nutritional composition, in some embodiments, from about 5 mg/100 kcal to about 75 mg/100 kcal. In some embodiments, DHA is present from about 10 mg/100 kcal to about 50 mg/100 kcal. In still some embodiments, DHA is present from about 15 mg/100 kcal to about 30 mg/100 kcal.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to such oils.

Furthermore, some embodiments of the nutritional composition may mimic certain characteristics of human breast milk. However, to fulfill the specific nutrient requirements of some subjects, the nutritional composition may comprise a higher amount of some nutritional components than does human milk. For example, the nutritional composition may comprise a greater amount of DHA than does human breast milk. The enhanced level of DHA of the nutritional composition may compensate for an existing nutritional DHA deficit.

In some embodiments the nutritional composition comprises sialic acid. Sialic acids are a family of over 50 members of 9-carbon sugars, all of which are derivatives of neuroaminic acid. The predominant sialic acid family found in humans is from the N-acetylneuraminic acid sub-family. Sialic acids are found in milk, such as bovine and caprine. In mammals, neuronal cell membranes have the highest concentration of sialic acid compared to other body cell membranes. Sialic acid residues are also components of gangliosides.

If included in the nutritional composition, sialic acid may be present in an amount from about 0.5 mg/100 kcals to about 45 mg/100 kcal. In some embodiments sialic acid may be present in an amount from about 5 mg/100 kcals to about 30 mg/100 kcals. In still other embodiments, sialic acid may be present in an amount from about 10 mg/100 kcals to about 25 mg/100 kcals.

The nutritional composition may also contain one or more prebiotics (also referred to as a prebiotic source) in certain embodiments. Prebiotics can stimulate the growth and/or activity of ingested probiotic microorganisms, selectively reduce pathogens found in the gut, and favorably influence the short chain fatty acid profile of the gut. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides. In some embodiments, the total amount of prebiotics present in the nutritional composition may be from about 0.1 g/100 kcal to about 1 g/100 kcal. In certain embodiments, the total amount of prebiotics present in the nutritional composition may be from about 0.3 g/100 kcal to about 0.7 g/100 kcal. Moreover, the nutritional composition may comprise a prebiotic component comprising polydextrose ("PDX") and/or galacto-oligosaccharide ("GOS"). In some embodiments, the prebiotic component comprises at least 20% GOS, PDX or a mixture thereof.

If PDX is used in the prebiotic composition, the amount of PDX in the nutritional composition may, in an embodiment, be within the range of from about 0.1 g/100 kcal to about 1 g/100 kcal. In another embodiment, the amount of polydextrose is within the range of from about 0.2 g/100 kcal to about 0.6 g/100 kcal. And in still other embodiments, the amount of PDX in the nutritional composition may be from about 0.1 mg/100 kcal to about 0.5 mg/100 kcal or about 0.3 mg/100 kcal. Without being bound by any particular theory, it is believed that PDX in combination with the neurologic component of the present disclosure, especially when containing ALA, may synergistically enhance brain development and/or neurogenesis.

If GOS is used in the prebiotic composition, the amount of GOS in the nutritional composition may, in an embodiment, be from about 0.1 g/100 kcal to about 1 g/100 kcal. In another embodiment, the amount of GOS in the nutritional composition may be from about 0.2 g/100 kcal to about 0.5 g/100 kcal.

In other embodiments, the amount of GOS in the nutritional composition may be from about 0.1 mg/100 kcal to about 1.0 mg/100 kcal or from about 0.1 mg/100 kcal to about 0.5 mg/100 kcal.

In a particular embodiment of the nutritional composition, PDX is administered in combination with GOS. In this embodiment, PDX and GOS can be administered in a ratio of PDX:GOS of between about 9:1 and 1:9. In another embodiment, the ratio of PDX:GOS can be between about 5:1 and 1:5. In yet another embodiment, the ratio of PDX:GOS can be between about 1:3 and 3:1. In a particular embodiment, the ratio of PDX to GOS can be about 5:5. In another particular embodiment, the ratio of PDX to GOS can be about 8:2.

In a particular embodiment, GOS and PDX are supplemented into the nutritional composition in a total amount of at least about 0.2 mg/100 kcal or about 0.2 mg/100 kcal to about 1.5 mg/100 kcal. In some embodiments, the nutritional composition may comprise GOS and PDX in a total amount of from about 0.6 to about 0.8 mg/100 kcal.

In one embodiment, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

If included in the composition, the amount of the probiotic may vary from about $1\times10^4$ to about $1.5\times10^{10}$ cfu of probiotic(s) per 100 kcal. In some embodiments the amount of probiotic may be from about $1\times10^6$ to about $1\times10^9$ cfu of probiotic(s) per 100 kcal. In certain other embodiments the amount of probitic may vary from about $1\times10^7$ cfu/100 kcal to about $1\times10^8$ cfu of probiotic(s) per 100 kcal.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

In some embodiments, the nutritional composition may include a source comprising probiotic cell equivalents. In included in the nutritional composition, the amount of the probiotic cell equivalents may vary from about $1\times10^4$ to about $1.5\times10^{10}$ cell equivalents of probiotic(s) per 100 kcal. In some embodiments the amount of probiotic cell equivalents may be from about $1\times10^6$ to about $1\times10^9$ cell equivalents of probiotic(s) per 100 kcal nutritional composition. In certain other embodiments the amount of probiotic cell equivalents may vary from about $1\times10^7$ to about $1\times10^8$ cell equivalents of probiotic(s) per 100 kcal of nutritional composition.

In some embodiments, the probiotic source incorporated into the nutritional composition may comprise both viable colony-forming units, and non-viable cell-equivalents.

In some embodiments, the nutritional composition includes a culture supernatant from a late-exponential growth phase of a probiotic batch-cultivation process. Without wishing to be bound by theory, it is believed that the activity of the culture supernatant can be attributed to the mixture of components (including proteinaceous materials, and possibly including (exo)polysaccharide materials) as found released into the culture medium at a late stage of the exponential (or "log") phase of batch cultivation of the probiotic. The term "culture supernatant" as used herein, includes the mixture of components found in the culture medium. The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In an embodiment, a culture supernatant is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) removing liquid contents from the culture supernatant so as to obtain the composition.

The culture supernatant may comprise secreted materials that are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the LGG batch-cultivation process. In some embodiments, the culture supernatant is harvested at a point in time of 75% to 85% of the duration of the exponential phase, and may be harvested at about ⅚ of the time elapsed in the exponential phase.

As noted, the disclosed nutritional composition may comprise a source of β-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalities, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, *Saccharomyces cerevisiae*, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

In some embodiments, the amount of β-glucan in the nutritional composition is between about 3 mg/100 kcal to about 17 mg/100 kcal. In another embodiment the amount of β-glucan is between about 6 mg/100 kcal to about 17 mg/100 kcal.

The nutritional composition may comprise in some embodiments β-1,3;1,6-glucan. The β-1,3;1,6-glucan can be derived from baker's yeast. The nutritional composition may comprise whole glucan particle β-glucan, particulate β-glucan, PGG-glucan (poly-1,6-β-D-glucopyranosyl-1,3-β-D-glucopyranose) or any mixture thereof.

The disclosed nutritional composition described herein, can, in some embodiments also comprise an effective amount of iron. The iron may comprise encapsulated iron forms, such as encapsulated ferrous fumarate or encapsulated ferrous sulfate or less reactive iron forms, such as ferric pyrophosphate or ferric orthophosphate.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 μm to 1500 μm, more preferably in the range of 10 μm to 300 μm.

If the nutritional composition is in the form of a ready-to-use product, the osmolality of the nutritional composition may be between about 100 and about 1100 mOsm/kg water, more typically about 200 to about 700 mOsm/kg water.

In certain embodiments, the nutritional composition is hypoallergenic. In other embodiments, the nutritional composition is kosher and/or halal. In still further embodiments, the nutritional composition contains non-genetically modified ingredients. In an embodiment, the nutritional formulation is sucrose-free. The nutritional composition may also be lactose-free. In other embodiments, the nutritional composition does not contain any medium-chain triglyceride oil. In some embodiments, no carrageenan is present in the composition. In other embodiments, the nutritional composition is free of all gums.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

Moreover, in some embodiments, the nutritional composition is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The nutritional composition of the present disclosure may be standardized to a specific caloric content, it may be provided as a ready-to-use product, or it may be provided in a concentrated form.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

In embodiments providing a nutritional composition for a child, the composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25, -dihydroxyvitamin D), vitamin E ($\alpha$-tocopherol, $\alpha$-tocopherol acetate, $\alpha$-tocopherol succinate, $\alpha$-tocopherol nicotinate, $\alpha$-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, $\beta$-carotene and any combinations thereof.

In embodiments providing a children's nutritional product, such as a growing-up milk, the composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to growing-up milks or to other children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the children's nutritional composition may contain between about 10 and about 50% of the maximum dietary recommendation for any given country, or between about 10 and about 50% of the average dietary recommendation for a group of countries, per serving, of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional composition(s) may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, grape and or grape seed extracts, apple extract, bilberry extract or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions may optionally include one or more emulsifiers that may be added for stability of the final product. Examples of suitable emulsifiers include, but are not limited to, lecithin (e.g., from egg or soy or any other plant and animal sources), alpha lactalbumin and/or mono- and diglycerides, and mixtures thereof. Other emulsifiers are readily apparent to the skilled artisan and selection of suitable emulsifier(s) will depend, in part, upon the formulation and final product.

The nutritional compositions may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, CITREM (citric acid esters of mono- and diglycerides of fatty acids), and mixtures thereof.

The present disclosure further provides method(s) for promoting brain and nervous system health by providing a nutritional composition comprising a neurologic component described herein to a target subject. Without being bound by any particular theory, it is believed that providing a nutritional composition comprising the neurologic component will support neurogenesis, and/or neuronal health and development.

In some embodiments the target subject may be a pediatric subject. Further, in one embodiment, the nutritional composition provided to the pediatric subject may be an infant formula. The neurologic component added to the infant formula may be selected from a specific source and concentrations thereof may be adjusted to maximize health benefits. In another embodiment of this method, the nutritional composition comprising a neurologic component that is provided to a pediatric subject is a growing up milk.

In another embodiment the nutritional composition may be provided to a target subject who has suffered, is currently suffering from, or is likely to suffer in the future from a brain and/or nervous system injury. In yet another embodiment, the nutritional composition comprising a neurologic component may be provided to any target subject to promote neuroprotection. In still other embodiments, the method is directed toward promoting neurogenesis by providing a nutritional composition comprising a neurologic component to a pregnant or lactating mother. Additionally, the nutritional compositions comprising a neurologic component described herein may provide a supplemental source of neurological nutrition to target subjects.

The present disclosure further provides a method for promoting neuronal health and/or development, as well as other benefits enumerated herein, and includes administering to a subject an effective amount of the nutritional composition of the present disclosure. In some embodiments, the nutritional composition may be expelled directly into a subject's intestinal tract and/or directly into the gut. In some embodiments, the composition may be formulated to be consumed or administered enterally.

The methods of the present disclosure directed toward providing the nutritional compositions described herein deliver enhanced neurological nutritional and health benefits to their target subjects. The disclosure of the methods for providing the nutritional composition described herein for a particular neurological illness or to a particular target subject are not to be limiting, instead they further serve as examples where administration of the nutritional composition described herein may be appropriate.

EXAMPLES

Examples are provided to illustrate the neurogenesis of the nutrients included in the neurologic component of the nutritional composition(s) described herein. Briefly, the neurogenesis capabilities of ALA were tested on human adipose derived stem cells ("hADSCs") by the procedure described herein. These examples should not be interpreted as any limitation on the nutritional compositions disclosed herein, but serve as illustrations of neurogenesis of the neurologic component. It is intended that the specification, together with the example, be considered to be exemplary only, with the scope and spirit of the disclosure being indicated by the claims which follow the examples. The procedures of U.S. patent application Ser. No. 13/408,485 filed by Kuang, et al. and U.S. patent application Ser. No. 13/408,490 filed by Kuang, et al., each of which filed on Feb. 29, 2012, may be suitable for practice of the present disclosure and are hereby incorporated by reference.

Example 1

This example describes the neurogenesis of hADSCs by ALA as compared to DHA and a negative control.

ALA was purchased from Sigma-Aldrich®, St. Louis, Mo. (Cat. #TI395-1G). ALA was diluted in 100% ethanol to 250 mg/mL and stored at −80° C.

hADSCs were purchased from Invitrogen, also known as Life Technologies, of Carlsbad, Calif., U.S.A., and were cultured as near confluent monolayers in 100 mm culture plates within a maintenance media consisting of Complete MesenPro RS medium with growth supplement and L-glutamine obtained from Invitrogen®. The process of culturing, passage, and seeding the hADSCs is described below.

The subculture of hADSCs was performed when cell culture reached confluence. To passage hADSCs, the following procedure is used: i) aspirate the Complete MesenPRO RS medium from the cells; ii) rinse the surface area of the cell layer with Dulbecco's phosphate buffered saline (DBPS) buffer by adding the DPBS to the side of the vessel opposite the attached cell layer and rocking the vessel back and forth several times; iii) remove the DPBS by aspiration and discard; iv) detach the cells by adding a sufficient volume of pre-warmed trypsin-EDTA solution without phenol red to cover the cell layer; v) incubate at 37° C. for approximately 7 minutes; vi) observe the cells under a microscope to determine if additional incubation is needed; vii) add 3 mL of the maintenance media to the plate, mix the cell suspension, add the suspension to a 15 mL centrifuge tube and centrifuge at 210 g for 5 minutes; viii) determine the total number of cells and percent viability using a hemacytometer; ix) add Complete MesenPRO RS medium to each vessel so that the final culture volume is 0.2 mL-0.5 mL per cm$^2$; x) seed the cells by adding the appropriate volume of cells to each vessel and incubate at 37° C., 5% $CO_2$ and 90% humidity; and xi) three or four days after seeding, completely remove the medium and replace with an equal volume of Complete MesenPRO RS medium.

Before seeding the passaged hADSCs on fresh culture plates, the surfaces of the culture ware are washed with sterile DPBS solution three times, followed by multiple rinses with sterile water. The first layer of coating is poly-L-ornithine. The coating is prepared by adding about 15 to about 20 g/mL of poly-L-ornithine and incubating at 37° C. for one hour. The plate is washed three times with DPBS, 15 minutes per wash. The second layer of coating is bovine plasma fibronectin. The fibronectin is diluted in DPBS from stock to 1:1000 and 500 µL is added to each well. The plate is left at room temperature for one hour. One final wash with 500 µL per well of DPBS is performed and the plate is used immediately.

The cells were then subjected to removal and reseeded at a density of $2\times10^4$ cells/ml ($1\times10^4$ cells/well) onto 24-well culture plates that contained a poly-L-ornithine and bovine plasma fibronectin coating.

Three days after seeding and priming; the culture medium was changed into neuronal differentiation medium. The culture plates were removed from the incubator and all procedures were conducted in a laminar flow hood. The culture medium was completely removed from each well. The hADSCs were then washed with sterile DPBS solution in an amount of about 1 ml per well, to remove excess culture medium. The DPBS solution was removed and replaced with neuronal differentiation medium. The formulation of the neuronal differentiation medium is such that neurogenesis would be attributed to the nutrient and not to the medium. The neuronal differentiation medium used was Neurobasal™ Medium, available from Invitrogen®, which comprises the following ingredients listed below in Table 1.

TABLE 1

Neurobasal ™ Medium

| Components | Molecular Weight | Concentration (mg/L) | mM |
|---|---|---|---|
| Amino Acids | | | |
| Glycine | 75 | 30 | 0.4 |
| L-Alanine | 89 | 2 | 0.0225 |
| L-Arginine hydrochloride | 211 | 84 | 0.398 |
| L-Asparagine-$H_2O$ | 150 | 0.83 | 0.00553 |
| L-Cysteine | 121 | 31.5 | 0.26 |
| L-Histidine hydrochloride-$H_2O$ | 210 | 42 | 0.2 |
| L-Isoleucine | 131 | 105 | 0.802 |
| L-Leucine | 131 | 105 | 0.802 |
| L-Lysine hydrochloride | 183 | 146 | 0.798 |
| L-Methionine | 149 | 30 | 0.201 |
| L-Phenylalanine | 165 | 66 | 0.4 |
| L-Proline | 115 | 7.76 | 0.0675 |
| L-Serine | 105 | 42 | 0.4 |
| L-Threonine | 119 | 95 | 0.798 |
| L-Tryptophan | 204 | 16 | 0.0784 |
| L-Tyrosine | 181 | 72 | 0.398 |
| L-Valine | 117 | 94 | 0.803 |
| Vitamins | | | |
| Choline chloride | 140 | 4 | 0.0286 |
| D-Calcium pantothenate | 477 | 4 | 0.00839 |
| Folic Acid | 441 | 4 | 0.00907 |
| Niacinamide | 122 | 4 | 0.0328 |
| Pyridoxine hydrochloride | 204 | 4 | 0.0196 |
| Riboflavin | 376 | 0.4 | 0.00106 |
| Thiamine hydrochloride | 337 | 4 | 0.0119 |
| Vitamin B12 | 1355 | 0.0068 | 0.000005 |
| i-Inositol | 180 | 7.2 | 0.04 |
| Inorganic Salts | | | |
| Calcium Chloride ($CaCl_2$) (anhyd.) | 111 | 200 | 1.8 |
| Ferric Nitrate ($Fe(NO_3)3''9H_2O$) | 404 | 0.1 | 0.000248 |
| Magnesium Chloride (anhydrous) | 95 | 77.3 | 0.814 |
| Potassium Chloride (KCl) | 75 | 400 | 5.33 |
| Sodium Bicarbonate ($NaHCO_3$) | 84 | 2200 | 26.19 |
| Sodium Chloride (NaCl) | 58 | 3000 | 51.72 |
| Sodium Phosphate monobasic ($NaH_2PO4$—$H_2O$) | 138 | 125 | 0.906 |
| Zinc sulfate ($ZnSO_4$—$7H_2O$) | 288 | 0.194 | 0.000674 |
| Other Components | | | |
| D-Glucose (Dextrose) | 180 | 4500 | 25 |
| HEPES | 238 | 2600 | 10.92 |
| Sodium Pyruvate | 110 | 25 | 0.227 |

ALA was added to individual wells at various concentrations in the serum-free medium. Pre-warmed serum-free medium contains Neural Basal medium with L-glutamine, 20 ng/mL of bFGF, 20 ng/mL of EGF and N2 supplement. See Table 2 below.

TABLE 2

N2 Supplement.

| Components | Molecular Weight | Concentration (mg/L) | mM |
|---|---|---|---|
| Proteins | | | |
| Human transferrin (Holo) | 10000 | 10000 | 1 |
| Insulin recombinant full chain | 5807.7 | 500 | 0.0861 |
| Other components | | | |
| Progesterone | 314.47 | 0.63 | 0.002 |
| Putrescine | 161 | 1611 | 10.01 |
| selenite | 173 | 0.52 | 0.00301 |

Treatments of ALA was tested at a concentration of 5 μg/ml. ALA was tested individually and compared to the positive control, DHA at 20 μM, and the negative control (no treatment) under phase contrast microscopy at 3 hours and 24 hours. The experiments were repeated in triplicate.

Figure 1B:
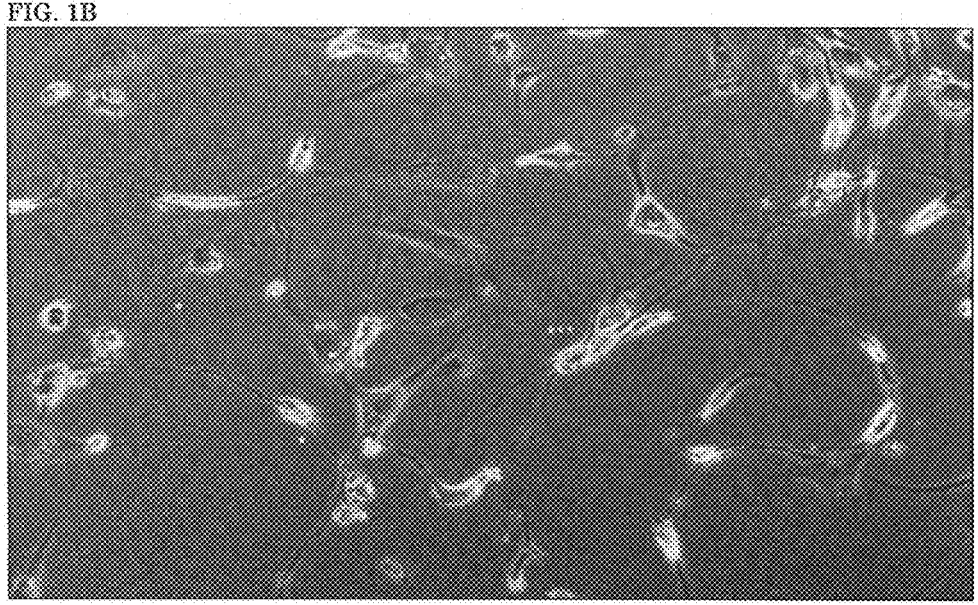
FIG. 1B is a phase contrast microscopy image of hADSCs forming morphologies that resembles bi-polar, tri-polar, and multi-polar neural cells.

After images were collected, data analysis and comparison was made to determine the effectiveness of ALA in promoting neurogenesis. Neuronal differentiation is determined by neuronal morphology. Some of these changes include shrinkage of the cytoplasm, and formation of axons and dendrite-like cytoplasmic projections (neurites). These changes begin with the cytoplasm of hADSCs retracting towards the nucleus to form contracted cell bodies with cytoplasmic extensions. Cells eventually develop a morphology that resembles bi-polar, tri-polar and multi-polar neuronal cells. See FIGS. 1A and 1B.

Figure 2A:
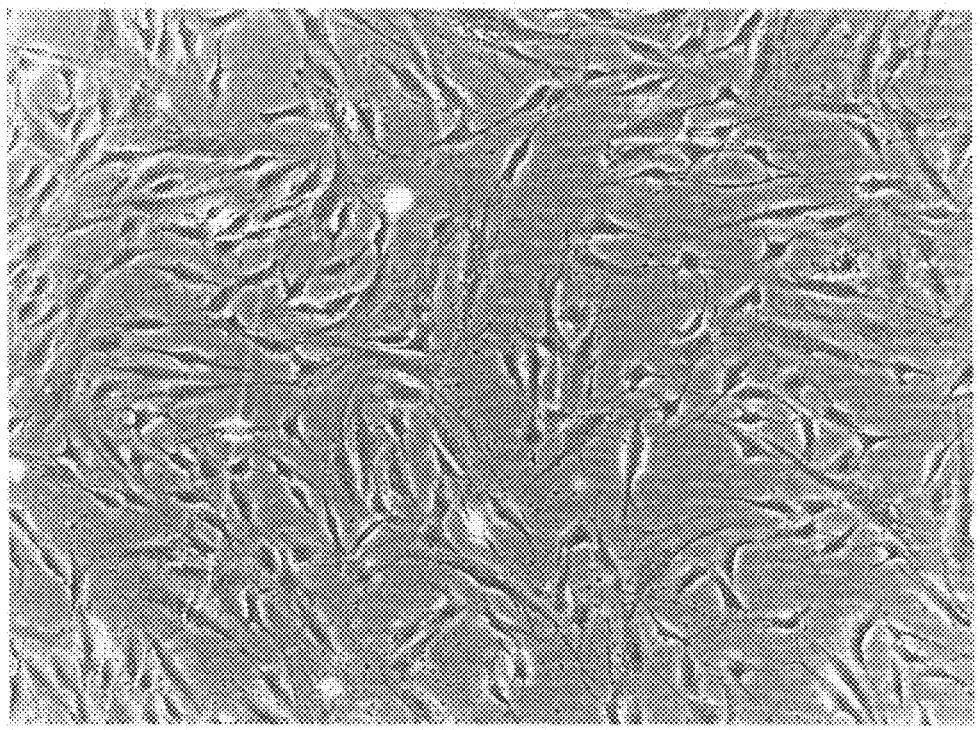
FIG. 2A is a phase contrast microscopy image of a control well containing hADSCs with no treatment of a neurologic component or DHA.

Generally, if the hADSCs display neuronal morphology this result is attributed to the neurogenesis capability of the neurologic component added, in this example ALA. For example, the hADSCs in the control wells with no treatment maintained their putative morphology as large, flat and spread cells on the culture surface, suggesting no obvious neurogenesis. See. FIG. 2A.

Figure 2B:
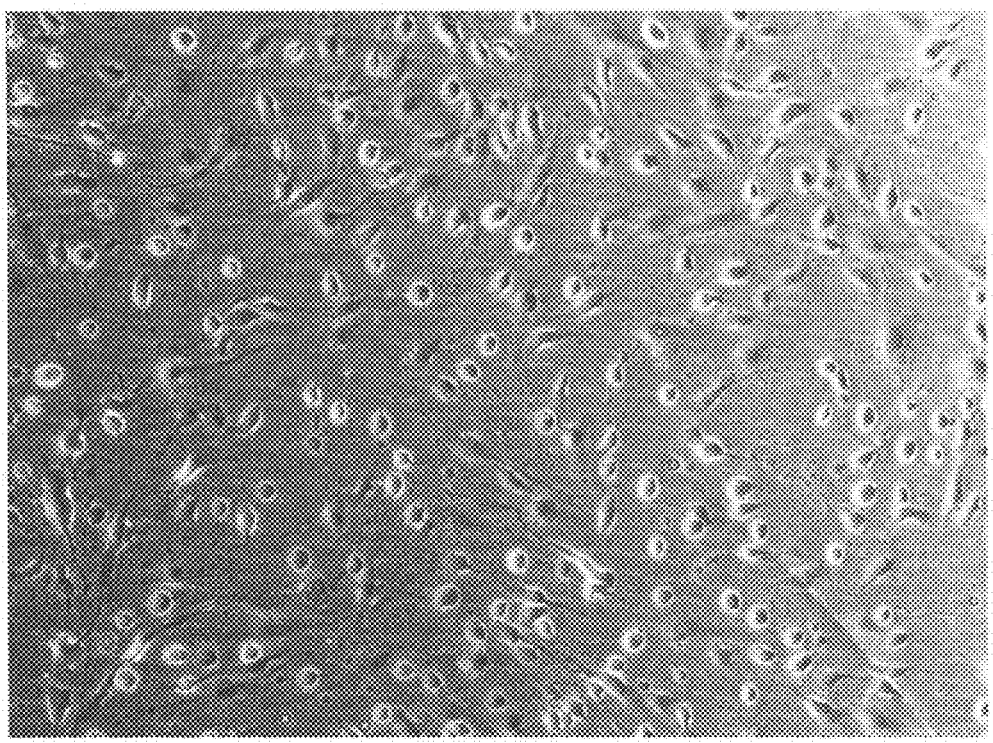
FIG. 2B is a phase contrast microscopy image of a control well containing hADSCs with treatment of DHA.
Figure 2C:
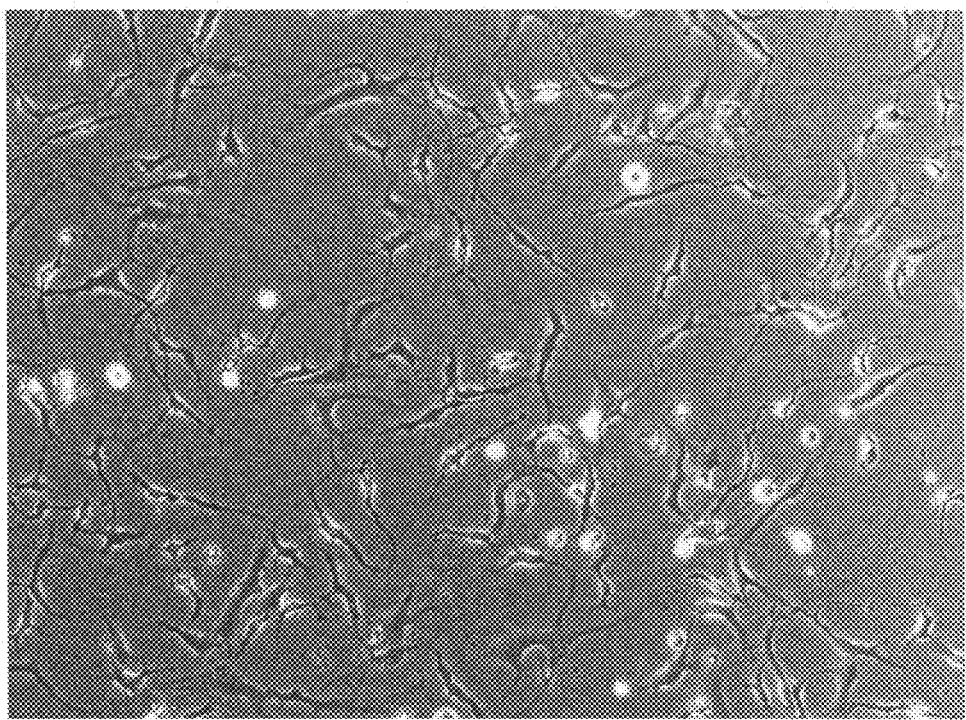
FIG. 2C is a phase contrast microscopy image of a control well containing hADSCs with treatment of ALA.

Noticeably, among the additions of ALA at 5 μg/ml demonstrated a strong effect to enhance neurogenesis as shown by the neuronal morphology displayed by the hADSCs in FIG. 2C. In light of these results, it was determined that ALA can serve as a naturally-occurring nutrient that possesses neurogenesis actions. The addition of ALA, also promoted neurogenesis when compared to the negative control. As illustrated, in FIG. 2C, ALA at a concentration of 5 μg/ml demonstrated neurogenesis, showing extensive neurite outgrowth, shrinkage of cytoplasm and neuronal differentiation of the hADSCs.

The additions of DHA at 20 μM to hADSCs as a positive control enhanced neuronal morphology of hADSCs when compared to the negative control. Further, in the presence of DHA at 20 μM, a few of the hADSCs changed dramatically from their putative morphology into neuronal cell morphology as the cytoplasm shrank and neurites began to protrude from the hADSCs. See FIG. 2B.

Moreover, as can be seen from comparing FIG. 2B, cells treated with DHA, to FIG. 2C, cells treated with ALA, the hADSCs treated with ALA showed obvious neuronal changes in terms of morphology, suggesting that ALA may have different neurogenesis pattern from that of DHA. ALA displayed a robust ability to promote neurogenesis in terms of neurite outgrowth when compared with DHA. Further, the neurite outgrowth produced by the treatment of ALA shows neurite extensions connecting with other neurite extensions to form neuronal network like structures. Thus ALA robustly promotes neurogenesis.

Moreover wells treated with ALA displayed less cell death overall, as compared to DHA, suggesting that ALA promotes neurogenesis robustly while having lower cellular toxicity. Compare FIG. 2B to FIG. 2C.

FORMULATION EXAMPLES

Table 1 provides an example embodiment of a neurologic component that may be incorporated or added to the nutritional compositions described herein. This example provides the amount of each ingredient to be included per 100 kcal serving of nutritional composition.

TABLE 1

Nutrition profile of an example neurologic component

| Nutrient | per 100 kcal | |
|---|---|---|
| | Minimum | Maximum |
| ALA (mg) | 3.7 | 37 |
| Zinc Sulfate (mg) | 0.1 | 2 |
| Allyl Sulfide (mg) | 1 | 170 |
| Allyl disulfide (mg) | 1 | 200 |
| Sulforaphane (mg) | 1.5 | 7.5 |
| Lactoferrin (mg) | 10 | 250 |

Table 2 provides an example embodiment of a nutritional composition according to the present disclosure and describes the amount of each ingredient to be included per 100 kcal serving.

TABLE 2

Nutrition profile of an example nutritional composition

| Nutrient | per 100 kcal | |
|---|---|---|
| | Minimum | Maximum |
| Protein (g) | 1.8 | 6.8 |
| Fat (g) | 1.3 | 7.2 |
| Carbohydrates (g) | 6 | 22 |
| Prebiotic (g) | 0.3 | 1.2 |
| DHA (g) | 4 | 22 |
| Beta glucan (mg) | 2.9 | 17 |
| ALA (mg) | 0.1 | 35 |
| Allyl Sulfide (mg) | 1 | 170 |
| Allyl disulfide (mg) | 1 | 200 |
| Sulforaphane (mg) | 1.5 | 7.5 |
| Probiotics (cfu) | $9.60 \times 10^5$ | $3.80 \times 10^8$ |
| Vitamin A (IU) | 134 | 921 |
| Vitamin D (IU) | 22 | 126 |
| Vitamin E (IU) | 0.8 | 5.4 |
| Vitamin K (mcg) | 2.9 | 18 |
| Thiamin (mcg) | 63 | 328 |
| Riboflavin (mcg) | 68 | 420 |
| Vitamin B6 (mcg) | 52 | 397 |
| Vitamin B12 (mcg) | 0.2 | 0.9 |
| Niacin (mcg) | 690 | 5881 |
| Folic acid (mcg) | 8 | 66 |
| Panthothenic acid (mcg) | 232 | 1211 |
| Biotin (mcg) | 1.4 | 5.5 |
| Vitamin C (mg) | 4.9 | 24 |
| Choline (mg) | 4.9 | 43 |
| Calcium (mg) | 68 | 297 |
| Phosphorus (mg) | 54 | 210 |
| Magnesium (mg) | 4.9 | 34 |
| Sodium (mg) | 24 | 88 |
| Potassium (mg) | 82 | 346 |
| Chloride (mg) | 53 | 237 |
| Iodine (mcg) | 8.9 | 79 |
| Iron (mg) | 0.7 | 2.8 |
| Zinc (mg) | 0.7 | 2.4 |
| Manganese (mcg) | 7.2 | 41 |
| Copper (mcg) | 16 | 331 |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the versions contained therein.

What is claimed is:

1. A method for promoting neuronal health and/or development in a pediatric subject, comprising administering a nutritional composition which comprises a carbohydrate source, a fat source, a protein source, a preservative, and a neurologic component, wherein the neurologic component comprises lactoferrin, zinc sulfate, alpha-lipoic acid, and from about 1.5 mg/100 kcal to about 7.5 mg/100 kcal sulforaphane.

2. The method of claim 1, wherein the alpha-lipoic acid is present in an amount from about 0.1 mg/100 kcal to about 35 mg/100 kcal.

3. The method of claim 1, wherein zinc sulfate is present in an amount of from about 0.1 mg/100 kcals to about 2 mg/100 kcals of nutritional composition.

4. The method of claim 1, wherein the neurologic component comprises allyl sulfide, allyl disulfide, and combinations thereof.

5. The method of claim 1, wherein the nutritional composition further comprises sialic acid.

6. The method of claim 1, wherein the nutritional composition further comprises a prebiotic.

7. The method of claim 1, wherein the nutritional composition further comprises docosahexaenoic acid.

8. The method of claim 1, wherein the nutritional composition is an infant formula.

9. The method of claim 1, wherein the nutritional composition further comprises a probiotic.

10. A method for promoting neuronal health and/or development comprising administering a nutritional composition which comprises per 100 kcal:
   (i) between about 6 g and about 22 g of a carbohydrate source;
   (ii) between about 1 g and about 7 g of a protein source;
   (iii) a preservative;
   (iv) between about 1.3 g and about 7.2 g of a fat source; and
   (v) a neurologic component comprising
      between about 1.5 mg to about 7.5 mg sulforaphane,
      between about 0.1 mg to about 35 mg alpha-lipoic acid,
      lactoferrin, and
      zinc sulfate.

11. The method of claim 10, wherein the nutritional composition further comprises per 100 kcal between about 0.3 g and about 1.2 g of prebiotic.

12. The method of claim 10, wherein the nutritional composition further comprises per 100 kcal between about 0.5 mg and about 45 mg of sialic acid.

13. The method of claim 10, wherein the nutritional composition further comprises between about 5 mg/100 kcal and 75 mg/100 kcal of docosahexaenoic acid.

14. The method of claim 10, wherein the neurologic component further comprises from about 1 mg to about 170 mg of allyl disulfide per 100 kcals of the nutritional composition.

15. The method of claim 10, wherein the nutritional composition further comprises from about 3 mg to about 17 mg of β-glucan per 100 kcals of nutritional composition.

16. A method of promoting neurogenesis in a pediatric subject, the method comprises administering a nutritional composition comprising a carbohydrate source, a fat source, a protein source, a preservative, and a neurologic component comprising lactoferrin from a non-human source, zinc sulfate, alpha-lipoic acid, allyl sulfide, and from about 1.5 mg/100 kcal to about 7.5 mg/100 kcal sulforaphane, to the pediatric subject.

17. The method of claim 16 wherein the nutritional composition further comprises sialic acid.

18. The method of claim 16, wherein the nutritional composition further comprises docosahexaenoic acid.

19. The method of claim 16, wherein the alpha-lipoic acid is present in an amount of from about 0.1 mg/100 kcal to about 37 mg/100 kcal.

20. The method of claim 16, wherein the nutritional composition comprises docosahexaenoic acid.

* * * * *